United States Patent [19]

Ohshima et al.

[11] 4,362,890
[45] Dec. 7, 1982

[54] PROCESS FOR THE PREPARATION OF UNSATURATED QUATERNARY AMMONIUM SALTS

[75] Inventors: Iwao Ohshima; Yasutaka Nakashima, both of Yokohama, Japan

[73] Assignees: Nitto Chemical Industry Co. Ltd.; Mitsubishi Rayon Co., Ltd., both of Tokyo, Japan

[21] Appl. No.: 213,331

[22] Filed: Dec. 5, 1980

[30] Foreign Application Priority Data

Dec. 27, 1979 [JP] Japan .................... 54-169314

[51] Int. Cl.$^3$ ............................................. C07C 67/52
[52] U.S. Cl. ............................. 560/222; 260/707
[58] Field of Search ............... 560/222; 159/45; 34/8; 260/707

[56] References Cited

U.S. PATENT DOCUMENTS

| | | | |
|---|---|---|---|
| 1,842,908 | 1/1932 | Lawrence | 260/707 |
| 2,688,045 | 8/1954 | Powers et al. | 260/707 |
| 3,400,548 | 9/1968 | Drayer | 260/707 |
| 3,405,209 | 10/1968 | Aagaard et al. | 260/707 |

FOREIGN PATENT DOCUMENTS 1538265  1/1979  United Kingdom .
1539257  1/1979  United Kingdom .

OTHER PUBLICATIONS

Perry, John H., (Ed.), "Chemical Engineers' Handbook", McGraw-Hill, Publ. 3rd Ed., 1950, pp. 863-870.
Chemical Engineering Catalog, 55th Ed., 1971, p. B-90.

*Primary Examiner*—Natalie Trousof
*Assistant Examiner*—L. Hendriksen

*Attorney, Agent, or Firm*—Cushman, Darby & Cushman

[57] ABSTRACT

A process for preparing an unsaturated quaternary ammonium salt represented by the general formula (I):

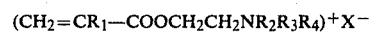

$$(CH_2=CR_1-COOCH_2CH_2NR_2R_3R_4)^+X^-$$

wherein $R_1$ is —H or —$CH_3$, $R_2$ and $R_3$ are —$CH_3$ or —$C_2H_5$, $R_4$ is —$CH_3$ or —$C_2H_5$, and X is Cl, Br or I, by reacting an unsaturated tertiary amine represented by the general formula (II):

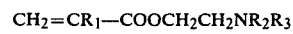

$$CH_2=CR_1-COOCH_2CH_2NR_2R_3$$

wherein $R_1$, $R_2$ and $R_3$ are as defined above, with a halogenated hydrocarbon in an aqueous medium, characterized in that:
 (i) the reaction is carried out at a concentration of the unsaturated tertiary amine in the aqueous medium of 78 to 91% by weight to produce the unsaturated quaternary ammonium salt in the aqueous medium of 82-93% by weight, and the reaction temperature is so controlled that no precipitation of the crystals of the unsaturated quaternary ammonium salt occurs, and
 (ii) the reaction product solution obtained is cooled by attaching it, either immediately or after mixing with the reaction product solution which has already been cooled to a temperature lower than that of said reaction product solution, in the form of a thin film onto a cooled glass-lined or chromium-plated solid surface to precipitate the unsaturated quaternary ammonium salt crystals to obtain the desired slurry.

11 Claims, 2 Drawing Figures

PROCESS FOR THE PREPARATION OF UNSATURATED QUATERNARY AMMONIUM SALTS

BACKGROUND OF THE INVENTION

1. Field of the Invention

This invention relates to a process for obtaining an aqueous slurry containing 82–93% by weight of an unsaturated quaternary ammonium salt (hereinafter referred to as quaternary salt) represented by the general formula (I):

$$(CH_2=CR_1-COOCH_2CH_2NR_2R_3R_4)^+X^-,$$

wherein $R_1$ is —H or —$CH_3$, $R_2$ and $R_3$ are —$CH_3$ or —$C_2H_5$, $R_4$ is —$CH_3$ or —$C_2H_5$, and X is Cl, Br or I, by reacting an unsaturated tertiary amine (hereinafter referred to as tertiary amine) represented by the general formula (II):

$$CH_2=CR_1-COOCH_2CH_2NR_2R_3,$$

wherein $R_1$, $R_2$ and $R_3$ are as defined above, with a halogenated hydrocarbon in an aqueous medium.

2. Description of the Prior Art

The polymers comprising a predominant amount of monomers represented by the general formula (I) are credited with high availability as a cationic flocculant, and they are widely utilized for clearing industrial and domestic waste water. The demand for such polymers is increasing keenly lately with aggrandizement of the scale of city sewage disposal in recent years.

Many reports have been made hitherto concerning a process for the preparation of these polymers. For instance, there have been proposed a method by which the monomers are polymerized in aqueous solution having a water content of not less than 40% by weight and the polymerized product is dried and then pulverized and a method by which precipitation polymerization or suspension polymerization is carried out in an organic solvent and after removing the organic solvent, the product is dried and pulverized. These methods, however, are not necessarily advantageous for the industrial applications because they require a drying device for removing a large volume of water or need the use of an organic solvent which requires care in its treatment because of the risk of ignition or explosion.

On the other hand, a method for obtaining a bulk polymer by adding to a monomer of the general formula (I) water in an amount of 7–18% by weight based on the weight of said monomer and polymerizing this mixture is disclosed, for instance, in British Pat. No. 1,539,257 (this technique is hereinafter referred to as ultra-high concentration polymerization technique). according to this method, a polymer as produced can be easily pulverized, so that neither drying step nor use of any organic solvent is required.

For obtaining an aqueous monomer slurry containing not less than 80% by weight of a quaternary salt represented by the general formula (I), there is usually employed a method by which a tertiary amine of the general formula (II) is reacted with a halogenated hydrocarbon in an organic solvent to precipitate the quaternary salt in the form of crystals and the precipitated crystals are removed by filtration and then adjusted to a desired concentration, or a method by which a tertiary amine of the general formula (II) is quaternized in aqueous solution at a concentration of less than 80% by weight and to the obtained quaternary salt solution are added the previously prepared quaternary salt crystals, for example, obtained in the manner described above, to adjust the concentration. These methods, however, require use of a large quantity of crystals: for example, in order to form a 90% by weight aqueous quaternary salt slurry from 1 kg of a 80% by weight aqueous quaternary salt solution by increasing its concentration, it needs to use additional 1 kg of crystals.

On the other hand, it is required to use an organic solvent such as acetonitrile, dimethylformamide or the like for the production of crystals, so that, as the matter of course, a device for removing or recovering the organic solvent is required when the process is performed on an industrial scale. Furthermore, because of involvement of a danger of fire or explosion, these organic solvents call for a substantial expense for the safety facilities.

Various methods have been reported for quaternization of tertiary amines in aqueous solution (see, for example, British Pat. No. 1,538,265). Also, many studies have been made on the stabilization method, and some effective polymerization inhibitors have been found (for example, see Japanese Patent Application Kokai (Laid-Open) No. 46,711/79).

In addition, it is known to inhibit the polymerization of a quaternary salt by adjusting the pH of the reaction mixture after quaternization reaction to 3–6 (for example, Japanese Patent Application Kokai (Laid Open) No. 36,620/77).

However, the solution of the quaternary salts of the general formula (I) obtained by quaternization in aqueous solution has a concentration of less than 80% by weight, and hence, the advantages of said ultra-high concentration polymerization technique cannot be derived from direct use of such quaternary salts.

The reason why the quaternary salt solution with an ultra-high concentration cannot be obtained is that, at the ordinary reaction temperatures for the quaternization reaction, i.e., at 25°–40° C., the quaternary salt concentration exceeds the solubility at saturation to cause precipitation of the crystals, with the result that scaling takes place, for example, on the cooling surface designed for removing the reaction heat, and such scaling causess various troubles such as imperfect cooling.

In the case of a reaction on a laboratory scale, it may be possible to avoid crystal-precipitation even at a concentration as high as 87%, if attention is paid to the stirring rate or cooling surface temperature, but this owes to the high supersolubility of the quaternary salts and it is difficult to maintain a stabilized reaction condition on an industrial scale.

Under such circumstances, a method has been proposed for quaternizing an aqueous solution containing a monomer of the general formula (II) at a concentration of at least 80% by weight (British Pat. No. 1,538,265), but according to this method, it is merely attempted to dissolve the crystals by adding water when the quaternary salt has exceeded the saturation point to separate out, and it is impossible by this method to obtain aqueous quaternary salt slurry of an ultra-high concentration such as provided in this invention.

As another method, it is conceivable to concentrate an aqueous quaternary salt solution having a concentration of less than 80% by weight by heating or under vacuum, but in order to concentrate, for example, a 80% by weight aqueous solution to a concentration of 90% by weight, it needs to evaporate more than half of water in the aqueous solution, and since the vapor pressure of the aqueous solution is low, a large-scale evaporation apparatus is necessitated. This is disadvantageous.

SUMMARY OF THE INVENTION

The present inventors have made further efforts for solving these problems and have consequently found that an aqueous quaternary salt slurry of an ultra-high concentration suitable to said ultra-high concentration polymerization technique can be obtained by performing the quaternization reaction under such conditions that the produced quaternary salt are always in the dissolved state and quickly cooling the obtained reaction product solution under the specific conditions.

According to the present invention, there is provided a process for preparing an unsaturated quaternary ammonium salt represented by the general formula (I):

$$(CH_2=CR_1-COOCH_2CH_2NR_2R_3R_4)^+X^-$$

wherein $R_1$ is —H or —$CH_3$, $R_2$ and $R_3$ are —$CH_3$ or —$C_2H_5$, $R_4$ is —$CH_3$ or —$C_2H_5$, and X is Cl, Br or I, by reacting an unsaturated tertiary amine represented by the general formula (II):

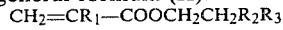
$$CH_2=CR_1-COOCH_2CH_2R_2R_3$$

wherein $R_1$, $R_2$ and $R_3$ are as defined above, with a halogenated hydrocarbon in an aqueous medium, characterized in that:

(i) the reaction is carried out at a concentration of the unsaturated tertiary amine in the aqueous medium of 78 to 91% by weight to produce the unsaturated quaternary ammonium salt at a concentration in the aqueous medium of 82–93% by weight, and the reaction temperature is so controlled that there takes place no precipitation of the crystals of the unsaturated quaternary ammonium salt, and (ii) the reaction product solution obtained is cooled by attaching it, either immediately or after mixing with the reaction product solution that has already been cooled to a temperature lower than said reaction product solution, in the form of a thin film onto a cooled glass-lined or chromium-plated solid surface to precipitate the unsaturated quaternary ammonium salt crystals, thereby forming the desired slurry.

Figure 1:
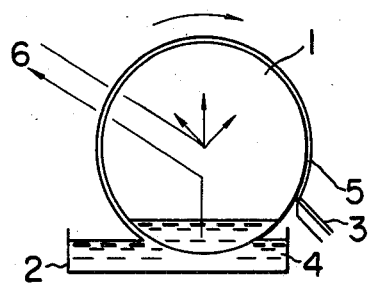
FIG. 1 is an illustration of an embodiment of this invention where the reaction product solution is cooled by a drum flaker type cooler having a single metal cylinder.

In the drawings:
1 . . . rotary drum,
2 . . . reaction roduct solution receiving tank,
3 . . . fixed knife,
4 . . . reaction product solution,
5 . . . slurry,
6 . . . cooling water.

DETAILED DESCRIPTION OF THE INVENTION

As typical examples of the unsaturated tertiary amines represented by the general formula (II), there may be used dimethylaminoethyl acrylate, dimethylaminoethyl methacrylate, diethylaminoethyl acrylate and diethylaminoethyl methacrylate. Examples of the halogenated hydrocarbons usable in this invention include methyl chloride, ethyl chloride, benzyl chloride, methyl bromide, ethyl bromide and ethyl iodide.

In order to perform the quaternization reaction while maintaining an ultra-high concentration of 82–93% by weight without any crystal precipitation throughout the reaction, it is necessary to control the temperature of the system to a temperature at which no crystal precipitation takes place, for example, 50°–90° C. It is not necessary to use a temperature as high as 50°–90° C. at the very beginning of the reaction; the initial phase of the reaction may be carried out at a conventional temperature, namely, 25°–40° C., and the temperature is elevated at a point slightly before the quaternary salt concentration exceeds the saturation concentration, thus completing the reaction always under the conditions that no crystal precipitation takes place. Since both the tertiary amines and the quaternary salts become more apt to spontaneously polymerize as the temperature rises, it is desirable to keep the reaction temperature as low as possible within the range where no crystal precipitation of quaternary salts occurs.

The saturation temperature of quaternary salts to water is about 78° C. at a concentration of 87% by weight in the case of a methyl chloride-quaternized dimethylaminoethyl methacrylate, but no crystal precipitation takes place even if the reaction temperature is lowered down to 65°–70° C. This is due to the extremely high supersolubility of the quaternary salts, and it is possible to lower the reaction temperature at the time of completion of the reaction to a temperature not more than 20° C. lower than the saturation temperature of the quarternary salts without causing any crystal precipitation. This is a new knowledge discovered by the present inventors, and this enables one to solve problems such as the above-mentioned polymerization or the like.

In the quaternization reaction, a halogenated hydrocarbon is usually used in excess relative to the quaternary amine, so that it is necessary to remove the excess halogenated hydrocarbon by a suitable means such as vacuum suction after the reaction.

The high-temperature reaction product solution thus obtained is cooled down to about 10°–30° C. and, as a most preferred form of treatment, subjected to an ultra-high concentration polymerization such as described in British Pat. No. 1,539,257. In the course of this cooling operation, crystals separate out in the reaction product solution, or the aqueous monomer solution. What is particularly important is that in case of performing the polymerization by said ultra-high concentration techniques, the monomer crystals would be sedimented during the polymerization induction period as the precipitated crystals become greater than a certain size, making it impossible to obtain a uniform polymer, and if the polymerization is carried out with the crystals left sedimented, the upper layer portion free from crystals becomes low in the quaternary salt concentration and hence the bulk polymer as produced cannot be easily pulverized.

The crystallizing devices commonly used in the chemical plants are usually designed to obtain as large crystals as possible so as to facilitate the dehydrating and drying operations after crystallization, so that these devices are not suited as cooling and crystallizing means for use in this invention.

Under these circumstances, the present inventors have found that the desired ultra-high-concentration aqueous slurry of micro-crystals can be obtained by cooling the reaction product solution by attaching it in the form of a thin film onto a cooled, glass-lined or chromium-plated solid surface.

The flaker type coolers are most suited for carrying out the said cooling operation of this invention, and among coolers of this type, there are coolers of the drum flaker, belt flaker and disc flaker types which are usually used for cooling and solidifying (flaking) the melts. Usually, a metal is used as the material for the coolers, but in this invention, it is necessary to use a cooler glass-lined or chromium-plated at the portion contacting with the reaction product solution for preventing the polymerization of the quaternary salt.

Figure 2:
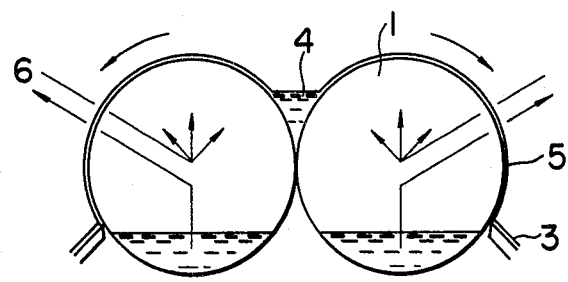
FIG. 2 is an illustration of another embodiment of this invention where the reaction product solution is cooled by a drum flaker type cooler having a pair of metal cylinders.

For example, in the case of the drum flaker type coolers such as shown in FIGS. 1 and 2, one or two metal cylinders through which cooling water is circulated are rotated at a low speed, and in the case where only one cylinder is used as in FIG. 1, the lower end of the cylinder is immersed in the reaction product solution, and in the case of using two cylinders as in FIG. 2, the reaction product solution is supplied to the area between the two cylinders which rotate in the opposite directions in contact with each other. The solution adheres in the form of a thin film to the drum surface and is cooled with rotation of the drum to precipitate the crystals, and the latter are scraped down by a fixed knife, and made into a slurry-like product. The cooling operation can be accomplished in a similar way in the case of the belt flaker or disk flaker type device, too.

The high-temperature solution which has just undergone the reaction may be stirred along with the already cooled reaction product solution, for example, the aqueous quaternary salt slurry at 10°–30° C., to cool the solution to 30°–50° C. and then subjected to the above-said cooling operation.

It is thus possible to obtain the desired aqueous quaternary salt micro-crystal slurry having an ultra-high concentraiton by quickly cooling the high-temperature reaciton product solution. Since the crystals attaching to the cooling surface are perfectly scraped away by the fixed knife, there is no likelihood of accumulation of crystals on the cooling surface to affect the cooling efficiency or cause other troubles such as polymerization in the long-time operation. Such effects cannot be obtained by any other methods.

The aqueous slurry obtained by the process of this invention can most favorably be used in the ultra-high concentration polymerization, but it can as well be used for the production of various polymers after diluting it into a solution having a concentration of less than 82% by weight.

This invention is further described below referring to Examples, but it is to be understood that the Examples are only by way of illustration and not by way of limitation.

EXAMPLE 1

52.7 kg of dimethylaminoethyl methacrylate (containing 2,000 ppm. of methylhydroquinone), 10.4 kg of water and 4 g of ammonium oxalate were charged into a glass-lined reactor having an inner capacity of 100 liters and equipped with a stirrer, a gas-blowing pipe, a thermometer and a cooling jacket, and then 17.4 kg of methyl chloride (equivalent to 1.03 moles based on the dimethylaminoethyl methacrylate) was blown into the mixture with stirring for a period of 4 hours.

The temperature of the reaction system was initially controlled at 35° C. by passing cooling water, and it was raised from approximately 3.0 hours after the commencement of the reaction, the reaction having been completed ultimately at the temperature of 70° C.

After removing the excess methyl chloride by vacuum suction, the reaction mixture was cooled and crystallized in a chromium-plated drum flaker (rotated at about 2.0 r.p.m.) having a diameter of 350 mm and a length of 500 mm, while passing cooling water at 5° C. through the drum flaker, to obtain an aqueous quaternary salt slurry at 25° C.

The crystals were very small and did not settle even after allowed to stand for about one hour.

EXAMPLE 2

80 kg of a reaction product solution at 70° C. obtained in the same way as in Example 1 was poured into 80 kg of the aqueous slurry obtained in Example 1, and the mixture was stirred for about 10 minutes. The temperature was 45° C.

Then the mixture was cooled to 25° C. by the same drum flaker as used in Example 1 to obtain an aqueous slurry in which about 30% by weight of crystals were contained.

The crystals were very small as in Example 1.

Comparative Examdple 1

About 3 kg of the aqueous slurry at 45° C. obtained in Example 2 was put into a glass-made separable flask having a glass-made cooling coil therein, and the slurry was cooled gradually with stirring by passing cooling water at 15° C. through the cooling coil. About 30 minutes later, it was observed that the crystals of a quanternary salt were attached firmly to the cooling coil surface. When cooling was continued till the temperature reached 25° C., there took place even more voluminous crystal deposition on the cooling coil surface.

The crystals of the slurry obtained were large in size and the crystals in the upper layer settled in a few minutes when the slurry was allowed to stand, and there could not be obtained a product conformable to the ultra-high concentration polymerization technique.

What is claimed is:

1. A process for preparing an unsaturated quaternary ammonium salt represented by the general formula (I):

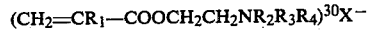
$$(CH_2=CR_1-COOCH_2CH_2NR_2R_3R_4)^{30}X^-$$

where $R_1$ is $-H$ or $-CH_3$, $R_2$ and $R_3$ are $-CH_3$ or $-C_2H_5$, $R_4$ is $-CH_3$ or $-C_2H_5$, and X is Cl, Br, or I, by reacting an unsaturated tertiary amine represented by the general formula (II):

$$CH_2=CR_1-COOCH_2CH_2NR_2R_3$$

wherein $R_1$, $R_2$ and $R_3$ are as defined above, with a halogenated hydrocarbon in an aqueous medium, characterized in that:

(i) the reaction is carried out at a concentration of the unsaturated tertiary amine in the aqueous medium of 78 to 91% by weight to produce the unsaturated quaternary ammonium salt at a concentration in the aqueous medium of 82–93% by weight, and the reaction temperature is elevated so that it reaches 65° to 90° C. at the time of completion of the reaction and so controlled that no precipitation of the crystals of the unsaturated quaternary ammonium salt occurs and (ii) the reaction product solution obtained is cooled by attaching it, either immediately or after mixing with the reaction product solution which has already been cooled to a temperature lower than that of said reaction product solution, in the form of a thin film onto a cooled glass-lined or chromium-plated solid surface to precipitate the unsaturated quaternary ammonium salt crystals to form the desired slurry.

2. The process according to claim 1, wherein the unsaturated tertiary amine represented by the general formula (II) is selected from the group consisting of dimethylaminoethyl acrylate, dimethylaminoethyl methacrylate, diethylaminoethyl acrylate and diethylaminoethyl methacrylate.

3. The process according to claim 1, wherein the halogenated hydrocarbon is selected from the group consisting of methyl chloride, ethyl chloride, benzyl chloride, methyl bromide and ethyl iodide.

4. The process according to claim 1, wherein the unsaturated tertiary amine represented by the general formula (II) is dimethylaminoethyl methacrylate and the halogenated hydrocarbon is methyl chloride.

5. The process of claim 4 wherein the elevated temperature is 70° to 90° C.

6. The process of claim 4 wherein the elevated temperature is 65° to 70° C.

7. The process according to claim 1, wherein the reaction temperature at the time of completion of the reaction is not more than 20° C. lower than the saturation temperature of the quaternary ammonium salt in the reaction system.

8. The process according to claim 1, wherein the reaction is carried out at a temperature of 25°–40° C. during the early phase of the reaction, and the temperature of the system is elevated to 50°–90° C. from shortly before the concentration of the unsaturated quaternary ammonium salt exceeds the saturation concentraiton.

9. The process according to claim 1 or 8 wherein the temperature of the reaction system is quickly lowered to the range of 10°–30° C. after the completion of the reaction.

10. The process according to claim 1, wherein the reaction product solution is cooled by using a flaker type cooler.

11. The process according to claim 8, wherein the flaker type cooler is drum type cooler.

* * * * *